(12) United States Patent
Fakhouri et al.

(10) Patent No.: US 11,813,198 B1
(45) Date of Patent: Nov. 14, 2023

(54) CIRCULAR CAPSULOTOMY INCISION TOOL

(71) Applicant: KING SAUD UNIVERSITY, Riyadh (SA)

(72) Inventors: Abdulaziz Saud Fakhouri, Riyadh (SA); Bandar Rashed Alnafisah, Riyadh (SA); Thamer Najer Alotaibi, Riyadh (SA); Saad Hamdan M. Alenezi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/117,381

(22) Filed: Mar. 3, 2023

(51) Int. Cl.
*A61F 9/007* (2006.01)
*A61B 17/00* (2006.01)

(52) U.S. Cl.
CPC ...... *A61F 9/00763* (2013.01); *A61F 9/00754* (2013.01); *A61B 2017/0023* (2013.01); *A61B 2017/00367* (2013.01)

(58) Field of Classification Search
CPC ............. A61F 9/00763; A61F 9/00754; A61B 2017/0023; A61B 2017/00367
See application file for complete search history.

(56) References Cited

U.S. PATENT DOCUMENTS

| | | |
|---|---|---|
| 4,766,897 A | 8/1988 | Smirmaul |
| 5,269,787 A | 12/1993 | Cozean, Jr. et al. |
| 6,165,190 A | 12/2000 | Nguyen |
| 6,379,370 B1 * | 4/2002 | Feinsod ............. A61F 9/00754 30/301 |
| 8,162,931 B2 | 4/2012 | Ben-Nun |
| 8,235,978 B2 | 8/2012 | Ben-Nun |
| 9,295,583 B2 | 3/2016 | Van Dalen et al. |
| 10,363,167 B2 | 7/2019 | Keller |
| 2019/0125582 A1 * | 5/2019 | Marchini ............ A61F 9/00754 |
| 2019/0380872 A1 | 12/2019 | Keller |
| 2022/0000665 A1 * | 1/2022 | Marchini ............ A61F 9/00754 |

FOREIGN PATENT DOCUMENTS

WO 2020/099192 A1 5/2020

OTHER PUBLICATIONS

ZEPTO, Aequus Pharmaceuticals Inc, https://zeptocapsulotomy.ca/technology/zepto, 2020.

* cited by examiner

*Primary Examiner* — Tan-Uyen T Ho
*Assistant Examiner* — Rachel S Highland
(74) *Attorney, Agent, or Firm* — Nath, Goldberg & Meyer; Richard C. Litman

(57) ABSTRACT

The first step for removal of cataracts generally is a capsulotomy—the removal of the anterior capsule of the eye lens. The circular capsulotomy incision tool provides a device that produces sharper cuts, with precise measurements, in an economical, reliable form without the need for complicated or expensive equipment, or extensive surgeon training or skill. The tool uses a resilient ring with a sharp cutting edge. The ring is collapsed, put in place through a corneal incision, and the original circular shape is allowed to return. The device uses a pulley mechanism to rotate the ring, enabling the cutting edge to reliably create a precisely edged capsulotomy.

9 Claims, 8 Drawing Sheets

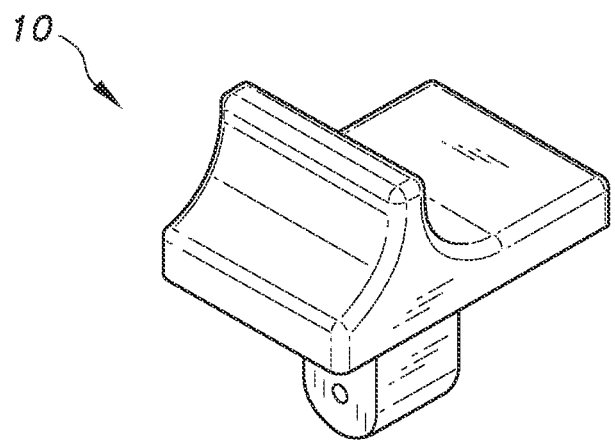
FIG. 8
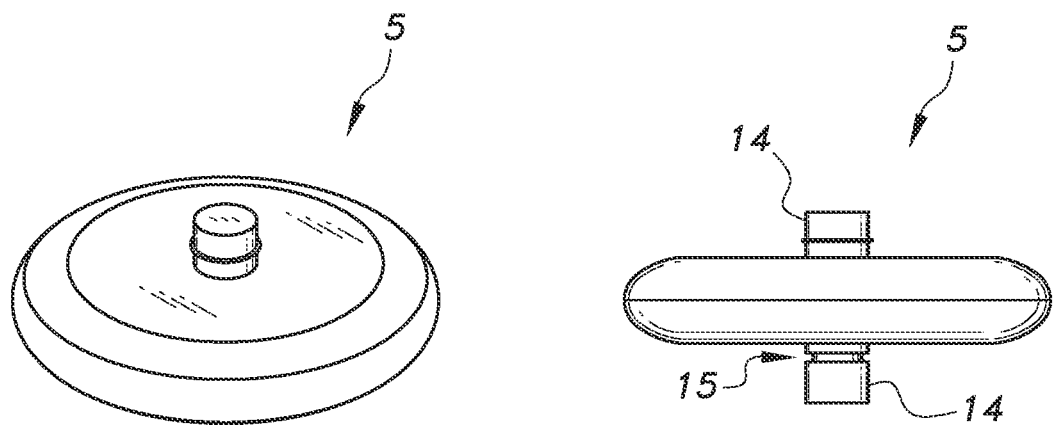
FIG. 9A
FIG. 9B

CIRCULAR CAPSULOTOMY INCISION TOOL

BACKGROUND

1. Field

The disclosure of the present patent application relates to a surgical instrument for ophthalmic surgeries, and particularly to a circular capsulotomy incision tool for performing a capsulotomy during cataract surgery.

2. Description of the Related Art

The human eye consists of many essential parts, including the cornea, aqueous humor, pupil, iris, lens, and retina. The cornea, which is the front clear portion of the eye, focuses the light on the retia through other optical components, mainly the cornea and lens. The light passes over the aqueous humor and through the pupil, which is the small opening in the eye controlled by the iris muscles.

The lens is located directly behind the pupil. The natural lens that humans are born with is a clear flexible structure made of transparent proteins called the crystalline lens. The lens focuses light towards the retina, which is located at the back of the eye.

The lens changes in shape based on the need of accommodation process, depending on an object's proximity to the eye, and is controlled by ciliary muscles through small fibers called zonules. The lens is encapsulated, and these zonules are attached to the capsule. The capsule is composed of two sides, anterior and posterior.

The quality of a person's vision depends on the transparency of the lenses in their eyes. In a healthy eye, the lens should be clear to pass the incident light without scattering and to focus the light properly onto the retina.

However, when the lens is cloudy, light scatters as it passes through the clouded lens. This prevents properly focusing light onto the retina. As a result, objects will appear hazy and blurry. See FIGS. 1A and 1B. Furthermore, a clouded lens may also result in decreased perception of color, presenting a "washed out" look. The effect is similar to when a viewer looks through something that is opaque, rather than transparent. This cloudiness is due to the build-up of proteins in the lens, which prevents light from passing through in an unscattered manner.

Cataracts can develop as a result of many factors, including aging, hypertension, diabetes, obesity, smoking, ultraviolet radiation exposure, previous eye surgery or injury, and heredity. In addition, cataracts can lead to glaucoma if not properly and promptly treated. Glaucoma is a disease caused by fluid (aqueous humor) build-up in the front part of the eye, which increases pressure in the eye, causing damage to the optic nerve. This leads to more permanent damage to the patient's sight.

A recent study done by the American Academy of Ophthalmology shows that more than 24 million Americans over the age of 40 have cataracts. According to another source, more than 50% of Americans developed cataracts by the age of 80. A study done in Saudi Arabia was conducted on 705 adults aged 18 years and older. The results showed that 166 out of the 705 subjects had visual impairment. Cataracts was the main cause of the visual impairment, where 51 out of the 166, or 30.7%, had cataracts.

According to the American Academy of Ophthalmology, around 40% of patients with cataracts and aged between 70 to 79 years old have had cataract surgery. In addition, more people are having cataract surgery each year. In recent years, cataract surgery is more affordable and more available than in the past. Cataract treatment is mostly done by surgical intervention. Generally, the natural clouded lens is replaced with an artificial one, called an Intraocular Lens (IOL).

Cataract surgery is usually done in three main steps, which are capsulotomy, phacoemulsification, and intraocular lens implanting. The ophthalmologist starts with creating an incision near the edge of the cornea, which is called a corneal incision. The incision is about 2.2 mm wide, and provides access for the following steps. In a capsulotomy, the anterior capsule of the lens is removed to create an opening to allow the next step, which is use of an ultrasound probe in the phacoemulsification step.

Phacoemulsification involves inserting the ultrasound probe inside the eye to break up and remove the crystalized proteins in the clouded lens via suction. After the capsulotomy and phacoemulsification, the intraocular lens (IOL) implantation takes place. A folded artificial lens is inserted through the same corneal incision onto the posterior capsule, where it unfolds, replacing the natural lens.

Traditionally, the capsulotomy involves a capsulorhexis procedure, also known as continuous curvilinear capsulorhexis (CCC). This manual technique utilizes forceps and/or a needle to excise part of the anterior lens capsule, using shear and stretch forces to extend the cut as needed and to facilitate removal of the anterior capsule of the lens.

The process starts by attempting to create a relatively circular incision on the top of the capsule. Ideally, the cut should be almost round, with a diameter of about 5.5 mm, well-centered, and overlapping the IOL to be implanted, around its circumference. The needle makes a slit on top of the anterior capsule, and the forceps are used to grasp the flap and manually rotate it, extending and tearing the slit to form a roughly circular incision, ultimately detaching the anterior capsule. This technique-requires a high degree of skill of the surgeon to be performed successfully. Unsuccessful capsulorhexis can lead to undesired complications, such as radial tear extensions when the tear moves in an unintended direction, and then sequelae of this complication, such as dropped lens in the vitreous, vitreous loss, or aphakia.

A more precise tool with less risk of complications clearly is desirable for performing a capsulotomy.

Another technology developed for performing a capsulotomy is the Femtosecond Laser-Assisted Cataract Surgery (FLACS). FLACS utilizes a femtosecond laser that emits optical pulses with a fixed duration of less than 1 picosecond. This technology has brought a new level of precision in performing certain steps in cataract surgery. These include the corneal incision, the capsulotomy, and the cataract fragmentation, which involves breaking down the cataract into smaller and softer pieces, facilitating easier suction using the ultrasound probe.

FLACS has advantages over the manual Capsulorhexis procedure. FLACS produces a more precise circular capsulotomy, with sharp edges and accurate diameter. However, FLACS is very expensive. A femtosecond laser device can cost about $500,000 or more. Additionally, there are service fees for the device, which will add about another 10% of the initial cost each year. Therefore, if cataract surgery is done using the FLACS method, it will likely significantly increase the cost of the operation, just to cover the costs of the equipment.

Another emerging technology that has been approved recently by the FDA is called Precision Pulse Capsulotomy (PPC). One commercial version of PPC is sold under the ZEPTO® brand. PPC is electrically operated by using an external console connected to a disposable handpiece with a capsulotomy tip. The capsulotomy tip is made of flexible nitinol ring and covered by a clear silicone suction cup. See FIG. 2. The PPC process uses delivery of a series of nanoelectrical pulse waves through the nitinol ring, vaporizing water molecules being trapped between the nitinol ring and the lens capsule. This causes instantaneous 360θ mechanical cleavage of the stretched capsule, resulting in a round, centered capsulotomy.

Unlike with FLACS, a surgeon using PPC does not need to deviate from a normal routine. Instead of using forceps and needle to perform capsulorhexis, the surgeon will simply use the PPC machine. The console costs around $10,000, and the disposable handpiece costs around $110-$160.

PPC offers many advantages, including cost efficiency. However, the PPC system uses vacuum and electrical ablation, such that the handheld piece uses a wired connection to the external console. The external wired connection may cause some disturbance and movement limitation during surgery. Furthermore, the capsulotomy ring is large in size, creating difficulties in maneuvering the ring inside the eye by the surgeon.

Again, a high precision, inexpensive tool requiring no external power connection and small in tip size would be desirable. Such a precise and simple capsulotomy tool would overcome limitations in existing technologies used in cataract surgeries. A tool that is easy to use for quick and precise capsulotomy will help in reducing difficulties and complications faced by ophthalmology surgeons. Further, making the instrument disposable from materials that are cost effective will help reduce some of the issues, such as bending or damaging the structure during handling and sterilization.

Thus, a circular capsulotomy incision tool solving the aforementioned problems is desired.

SUMMARY

The circular capsulotomy incision tool includes a collapsible ring with a sharp cutting edge. The ring has a loop of string, wire, or other filament wrapped around it and a pushing rod inserted through it. The pushing rod extends across the diameter of the ring and is fixed to the ring at its far end. A button is mounted on a handle of the tool and is designed to be operable by the surgeon using only one hand. By pushing the button forward, the pushing rod moves forward. The ring deforms, stretching in the direction of the pushing rod, with its width correspondingly collapsing. In this thin state, the collapsed ring can be inserted through an incision made in the corner of the eye and be placed adjacent the anterior capsule of the lens. By moving the button back to its original position, the ring expands to its original circular shape, and then by rotating a wheel mounted on the handle, which is fixed to the filament as a pulley wheel, the ring rotates, forming a perfectly circular incision about the anterior capsule.

These and other features of the present disclosure will become readily apparent upon further review of the following specification and drawings.

BRIEF DESCRIPTION OF THE DRAWINGS

FIG. 7A is a section view of the push rod sleeve of the tool of FIG. 3, showing internal structure of the sleeve.

FIG. 7B is a perspective view of the push rod sleeve of FIG. 7A.

FIG. 8 is a perspective view of the slide button of the tool of FIG. 3, which is mounted at the distal end of the housing.

FIG. 9A is a perspective view of the roller of the tool of FIG. 3, which is mounted in the distal end of the housing.

FIG. 9B is a side view of the roller of FIG. 9A.

Similar reference characters denote corresponding features consistently throughout the attached drawings.

DETAILED DESCRIPTION

The circular capsulotomy incision tool enables an economical, precise capsulotomy in a simple, reliable, consistent manner. The components required to perform capsulotomy are fully attached to a one handheld tool that operates mechanically, with no need for external attachments or wires, enabling free range of movement.

The circular capsulotomy incision tool is a handheld device that include a collapsible, resilient ring with a sharp cutting edge. The ring has a loop of string, wire, or other flexible filament wrapped around it, and a pushing rod inserted through it. The pushing rod extends across the diameter of the ring and is fixed to the ring at its far end. A button is mounted on a handle of the tool and linked to the push rod, being operable by the surgeon using only one hand. By pushing the button forward, the pushing rod moves forward. The ring deforms, stretching in the direction of the pushing rod, with its width correspondingly collapsing. In this stretched and elongated state, the collapsed ring can be inserted through an incision made through the cornea in the corner of the eye and placed adjacent the anterior capsule of the lens. By moving the button back to its original position, the ring resiliently expands to its original circular shape, and then by rotating a wheel mounted on the handle, operating as a pulley wheel, the flexible filamentous loop rotates the ring, forming a perfectly circular incision about the anterior capsule. The anterior capsule is removed, the clouded lens is fragmented and removed by an ultrasound suction probe (phacoemulsification), which is inserted through the capsulotomy incision. Then a new intraocular lens is folded and inserted in front of the posterior capsule, where it expands and is retained in the capsule through the circular capsulotomy incision, which is smaller in diameter than the new expanded intraocular lens.

The tool may be prepared in a disposable manner, using high quality, inexpensive, biocompatible materials that help to avoid some of the issues that otherwise may occur during sterilization, such as damaging capsulorhexis tools. Many of the components of the prototype, for example, were made from polyurethane and polylactic acid by 3D printing.

Figure 1A:
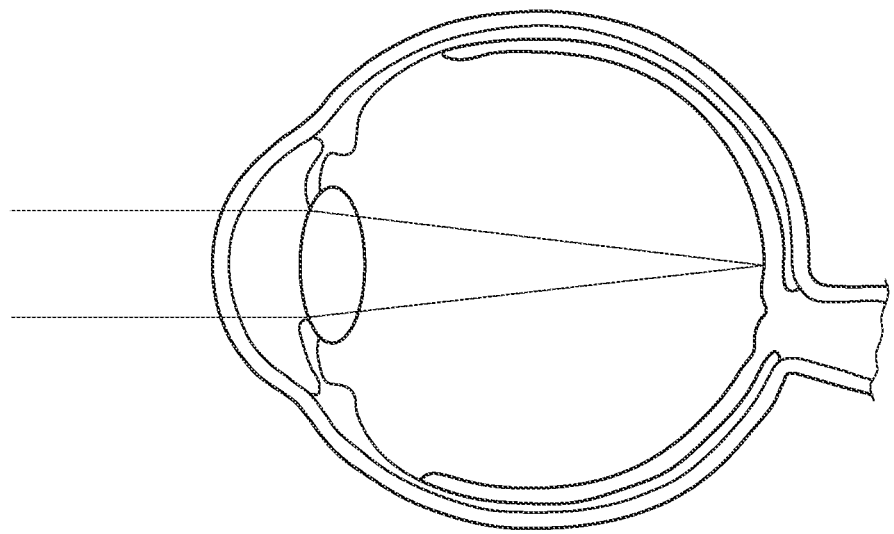
FIGS. 1A and 1B are schematic diagrams showing light entering a healthy lens being focused on the retina (FIG. 1A) and light entering a lens affected by cataracts and being scattered in different directions in the eye FIG. 1.
Figure 1B:
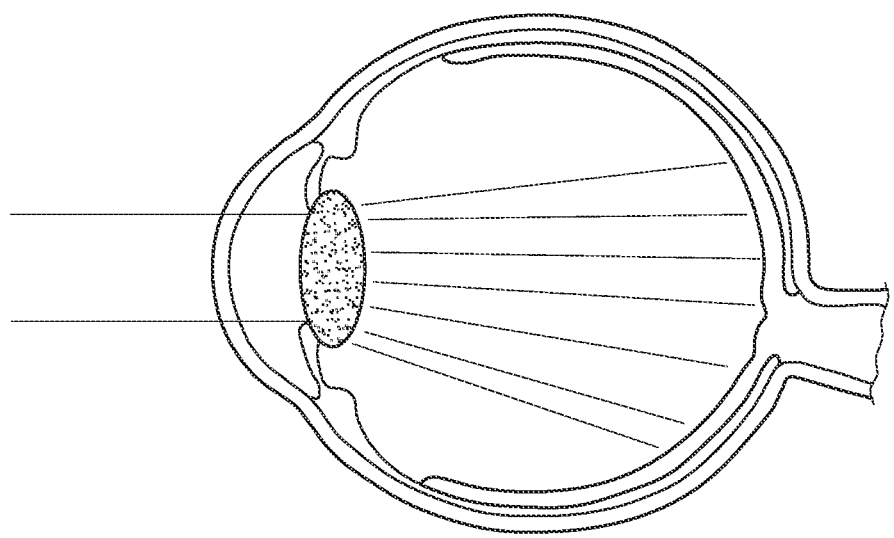
Figure 2:
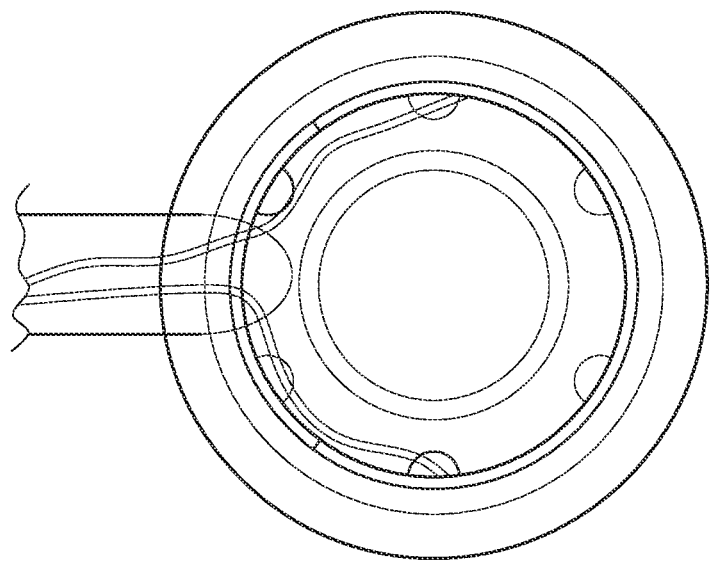
FIG. 2 is a schematic diagram of the tip of a ZEPTO® capsulotomy device of the prior art having a flexible nitinol ring covered by a clear suction cup.
Figure 3:
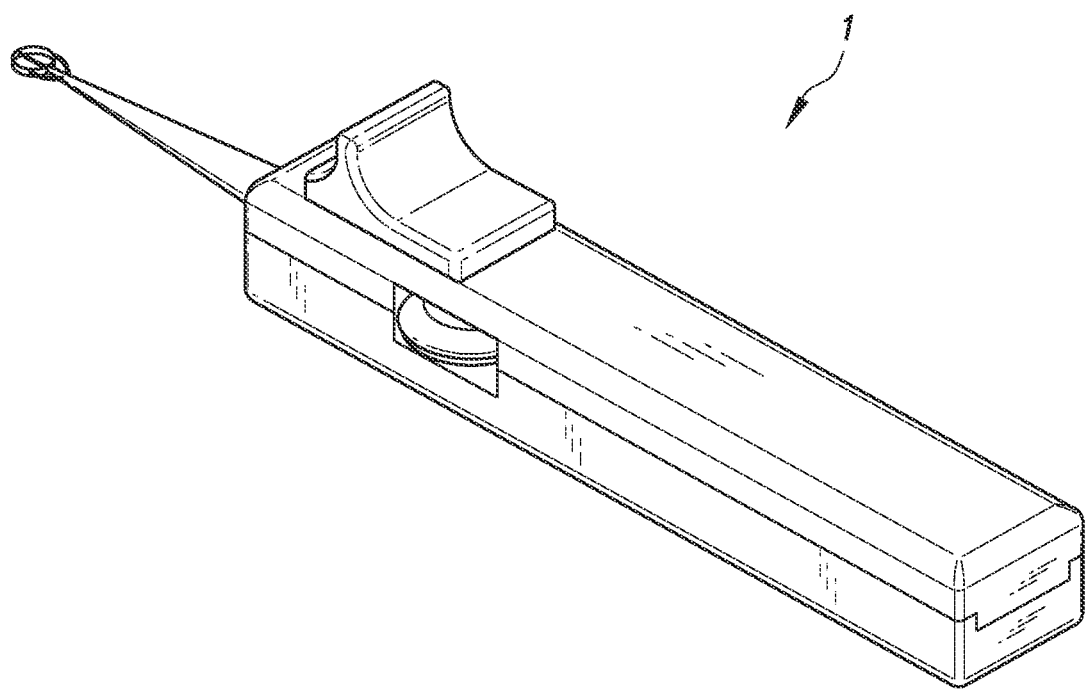
FIG. 3 is a perspective view of a circular capsulotomy incision tool.

As shown in FIGS. 1-10B, the circular capsulotomy incision tool 1 is small in size, fitting perfectly in the surgeon's hand, and light in weight, providing ease of use. The present device is easy to use, requiring less surgeon skill to perform accurate, reliable capsulotomy procedures. The tool 1 includes eight individual parts, including the retractable ring 2, housing 3, push rod sleeve 4, roller 5, string 6, push rod 7, and sliding button 10, as shown in FIG. 3.

Figure 4A:
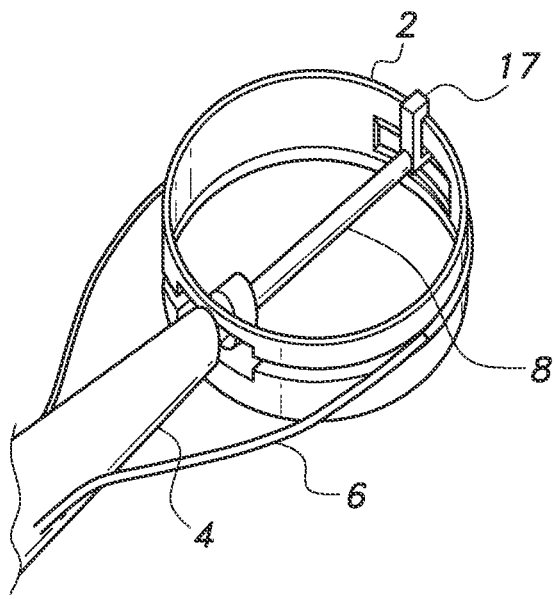
FIG. 4A is a partial perspective view of the tool of FIG. 3, showing the ring with the cutting blade disposed at the distal ends of the push rod and the rod sleeve before extension of the pushing rod and collapse of the ring.
Figure 4B:
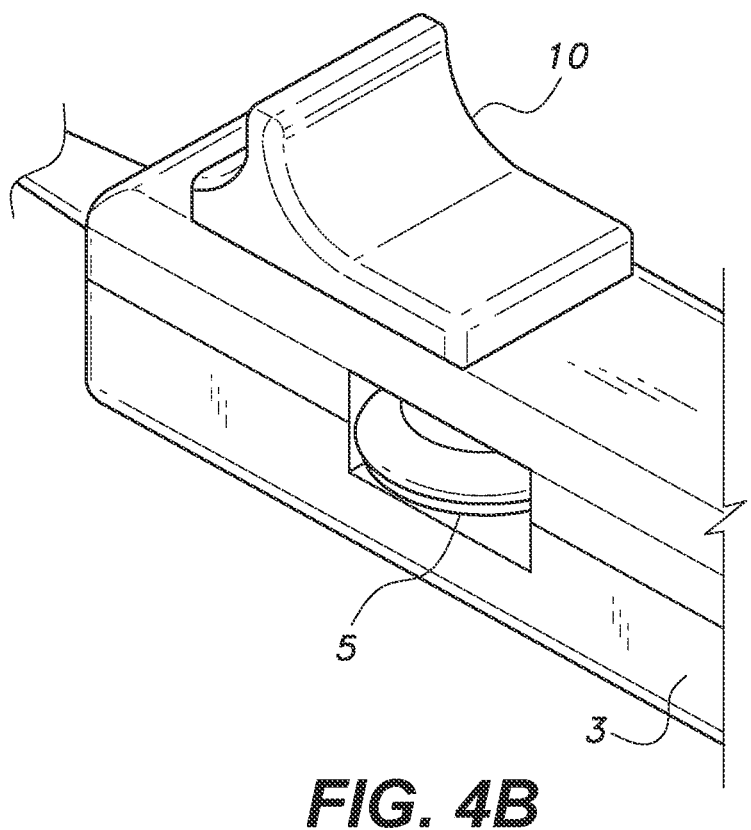
FIG. 4B is a partial perspective view of the tool of FIG. 3 showing the slide button for extending the push rod and the roller or pulley wheel for rotating the ring, both being mounted on or in the distal end of the housing.
Figure 5:
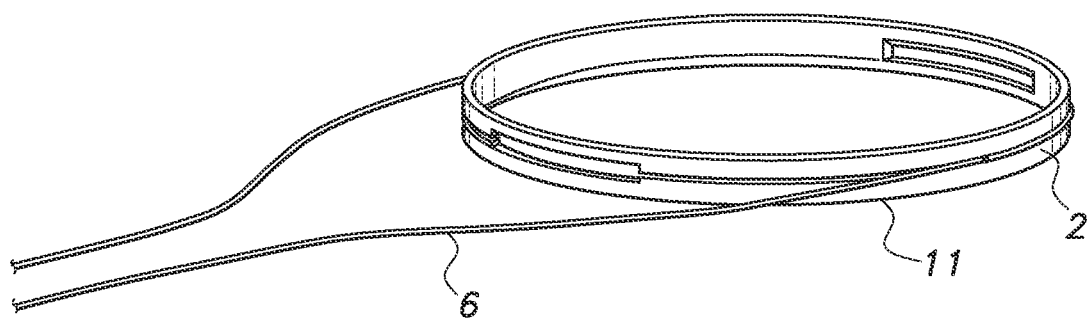
FIG. 5 is a perspective view of the ring of the tool of FIG. 3 with a flexible filament, such as a string or wire, looped around the ring.
Figure 6A:
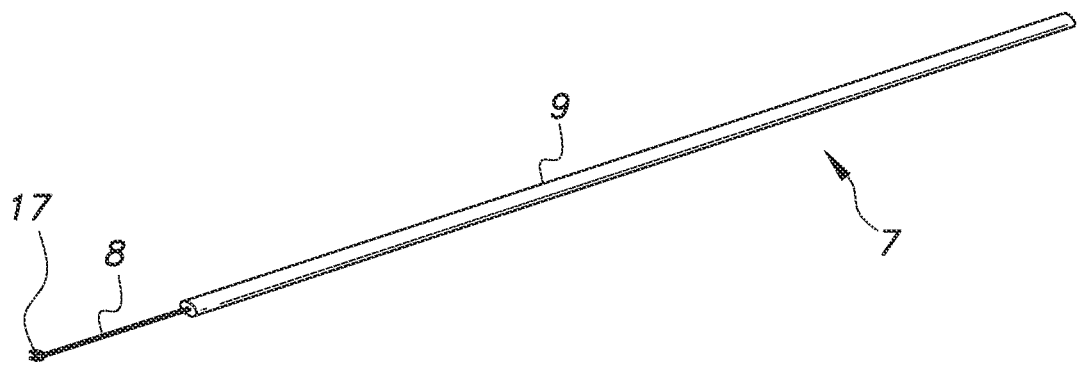
FIG. 6A is a perspective view of the push rod of the tool of FIG. 3, showing a C-shaped distal end that connects to the ring when extended by operating the slide button.
Figure 6B:
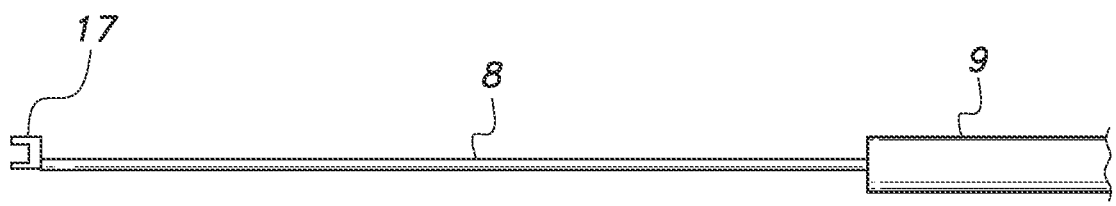
FIG. 6B is a side view of the push rod of FIG. 6A, showing the C-shaped distal end that connects to the ring when extended by operating the slide button.
Figure 7C:
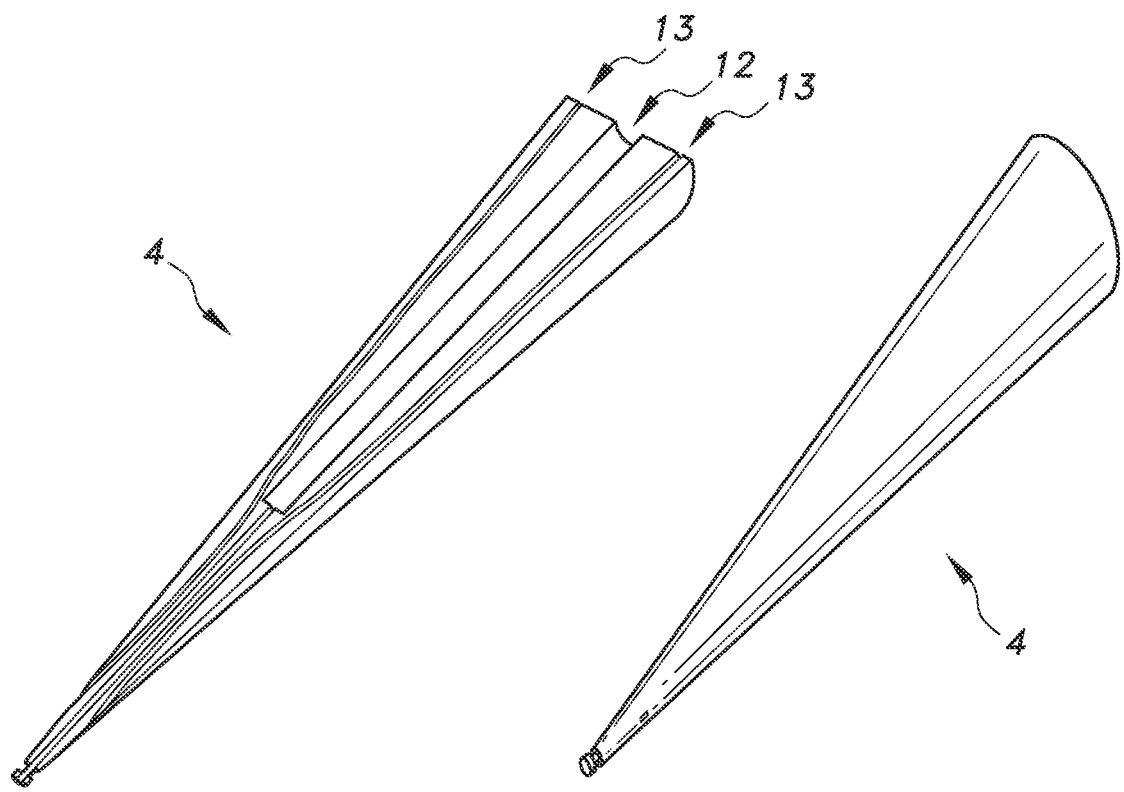
FIG. 7C is a partial perspective view of the sleeve of FIG. 7A, showing the annular notch that hooks into one of the arcuate slots defined in the ring.
Figure 7C:
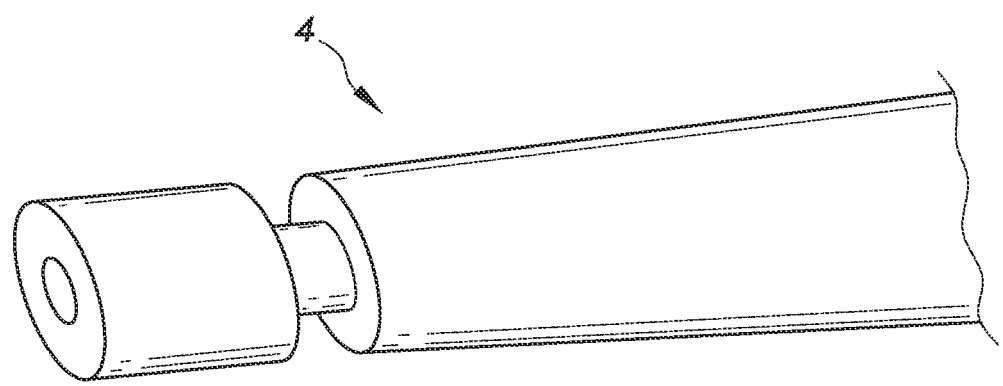
Figure 10A:
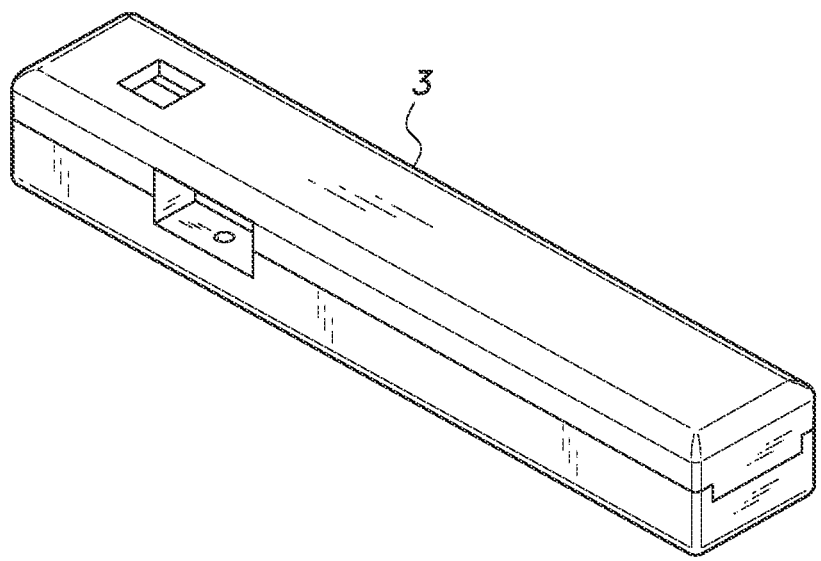
FIG. 10A is a perspective view of the housing of the tool of FIG. 3.
Figure 10B:
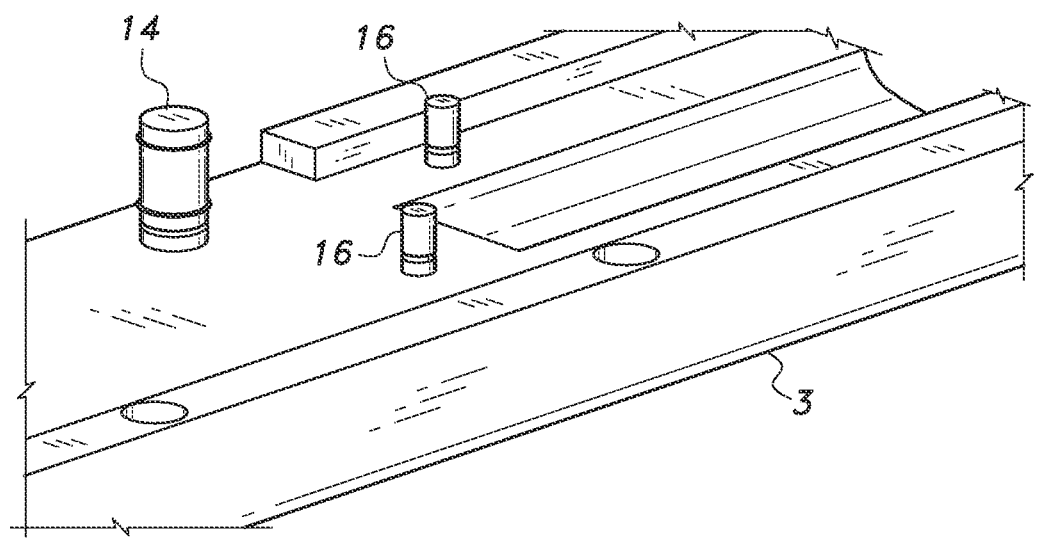
FIG. 10B is a perspective view in section of the housing of FIG. 10A, showing a portion of the internal structure of the housing.

The retractable ring 2, with a sharp cutting edge on one side 11, rotates back and forth to provide an oscillation movement by manual rotation of the roller (pulley wheel) 5, allowing the sharp cutting edge 11 to produce the capsulotomy cut, as shown in FIGS. 4A and 5. A standard diameter for the capsulotomy cut is about 5.5 mm in diameter, but the practitioner can determine whether a different diameter size may be warranted for a particular patient or procedure.

The string 6 (or wire or other elongated flexible filament) is wrapped around both the retractable ring 2 and the roller 5, so that turning the roller 5 rotates the string 6, thereby rotating (or oscillating, with a back and forth motion) the retractable ring 2. The oscillation results from moving the roller 5 back and forth, causing the retractable ring 2 to rotate in a back and forth motion. The string 6 or wire may have a thickness, for example, of 0.1 mm in diameter. See FIGS. 4A, 4B, 5, 9A, and 9B.

The push rod 7 has a larger-diameter portion 9 connected to the sliding button 10, and a smaller-diameter portion 8 having, for example, a C-shaped end 17 to contact and connect with the distal end of the retractable ring 2. See FIGS. 6A, and 6B, and FIG. 4A. The push rod 7 may be, for example, 74 mm in length. The larger-diameter portion 9 of the push rod 7 may be, for example, 1.4 mm in diameter and 64 mm in length, while the smaller-diameter portion 8 of the push rod 7 may be, for example, 0.29 mm in diameter and 11 mm in length.

The push rod sleeve 4 attaches to the housing 3 at one end, and to the retractable ring 2 at the other end. The push rod sleeve 4 functions as a tunnel or pathway for the push rod 7 and the string 6 from the housing 3 to the retractable ring 2. See FIGS. 7A and 7B. The push rod sleeve 4 has three openings or tunnels from one end to the other, including one large opening 12 usually roughly through the center of the push rod sleeve 4, having a diameter of, for example, 1.6 mm on the end closest to the housing 3, and then narrowing to, for example, 0.32 mm in diameter on the end that attaches to the retractable ring 2. This double-sized tunnel through the push rod sleeve 4 serves to house the push rod 7, fitting the smaller and larger diameter portions of the push rod 7. See FIG. 7A. The other two openings or string tunnels 13 through the push rod sleeve 4 are typically placed closer to lateral sides of the push rod sleeve 4, for example, with a diameter of 0.2 mm and total length of 46 mm. These openings or string tunnels 13 house and act as a pathway for the string 6 or wire.

The push rod sleeve 4 has, for example, a length of 51 mm, and maximum diameter of 8 mm near the housing 3, with the diameter decreasing gradually to 1.6 mm in diameter near the retractable ring 2.

The sliding button 10 is responsible of moving the push rod 7 to collapse and expand the cutting ring 2 via a sliding movement of the sliding button 10, with an area of, for example, 60 mm$^2$ to comfortably fit the user's thumb. See FIG. 8.

The roller 5 is rotated by hand in one direction or in an alternating fashion, moving the string or wire 6 similarly, one way or the other, or both. This causes the retractable ring 2 and its sharp cutting edge 11 to move in one direction or the other (clockwise or counterclockwise), or in an oscillatory manner, thus allowing the sharp cutting edge 11 to produce the desired capsulotomy incision. See FIGS. 4B, 5, 9A, 9B, 10A, and 10B. The roller 5 may have, for example, a diameter of 19.5 mm, and a total height of 5.93 mm. The roller 5 also may have an axle or rod 14 with a groove 15 for seating the string or wire 6 to facilitate moving the string or wire 6 by rotating the roller 5, producing the desired action from the retractable ring 2 and its sharp cutting edge 11.

The housing 3 contains the sliding button 10, and the roller 5, and helps guide the string or wire 6 looped around the roller 5 and the retractable ring 2. See FIGS. 10A, 10B. The housing 3 may contain the axle or rod 14 for the roller 5. The housing 3 may also contain one or more guides 16 to help align the string appropriately within the housing 3 as it approaches or leaves the roller 5. See FIG. 10B. The housing 3 may be, for example, 134 mm in length, and 16 mm in height, typically fitting easily and comfortably in the user's hand.

The circular capsulotomy incision tool uses mechanical manipulation to perform a capsulotomy, solving several of the limitations that exist in current methods. During cataract surgery, the user will first start by creating an incision near the edge of the cornea, typically about 2.2 mm in width. The circular capsulotomy incision tool is then used. The user will push forward the sliding button 10, moving the push rod 7 forward generally to the maximum allowed displacement, such as, for example, 4.3 mm. This displacement of the push rod 7 will stretch the resilient ring 2 with the cutting edge 11 to collapse to an elongated, narrow shape.

After the retractable ring 2 is collapsed, the retractable ring 2 is ready to be inserted through the corneal incision. The retractable ring 2 is inserted through the corneal incision in a collapsed state, and the user will then pull the sliding button backward, causing the ring 2 to be resiliently expand to regain its circular shape (generally about 5.5 mm in diameter). The cutting edge 11 of the ring 2 must be centered and properly placed above the anterior capsule of the lens.

The roller 5 (or pulley wheel) is connected to the ring 2 by the string or wire 6 that controls the rotary movement of the cutting edge 11. Oscillating the cutting edge 11 by alternately moving the roller 5 back and forth in clockwise/counterclockwise rotary movements will create a precisely edged capsulotomy.

Currently, this process is manually performed by the surgeon utilizing a forceps and a needle. Instead, here, and in stark contrast to prior art methods, the design of the capsulotomy device, with the pulley-type rotation and the push rod operable deformation of the retractable ring, provide an elegant, mechanical, inexpensive, but reliable and accurate circular capsulotomy, without the need for a highly skilled surgeon, or expensive, complicated, or encumbered equipment.

Additional embodiments and variations are readily available. For example, one embodiment would include a needle or blade at the tip of the C-shaped push rod end. The needle or blade could be used to create the corneal incision, providing access to the lens capsule. Another embodiment could use a different mechanism to attach the roller to the housing.

Ideally, the circular capsulotomy incision tool is made of medical-grade, biocompatible materials. The materials used should be cost-effective, allowing the device to be both at least partially disposable and affordable.

For the retractable ring, the material used should be biocompatible, resilient, and flexible, with the shape memory to allow it to resume its normal shape once released by the collapsing mechanism, as well as to withstand the force exerted by the push rod.

One option for a substance that satisfies these requirements is nitinol material (nickle-titanium alloy). Unlike other metal materials, it has an excellent shape memory function, which enables it to recover back to its original shape after being deformed. This is due at least in part to the application of high temperature during the manufacturing process. Nitinol also has good heat and corrosion resistance, high strength, thermal and fatigue resistance, and excellent biocompatibility. Nitinol has been used in many other applications in the medical field, such as in cardiovascular stents.

As for the push rod and the push rod sleeve, one option is stainless steel, such as 316L Stainless steel. 316L Stainless steel has high corrosion resistance, and is very affordable, while being easy to fabricate.

For the sleeve, sliding button, and/or roller, one option is to use a plastic polymer for these components. For example, acrylonitrile butadiene styrene (ABS) is a good option, as it has low production costs and ease of fabrication.

The string or wire could also be made of a plastic material. For example, polypropylene is a good example for use as the string or wire. Polypropylene also already is used in medical suturing, and is elastic, tough, and relatively inexpensive.

It is to be understood that the circular capsulotomy incision tool is not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A circular capsulotomy incision tool, comprising:
a housing having a distal end;
an elongated push rod having a proximal end slidably disposed in the housing and a distal end extending from the distal end of the housing;
a resilient, collapsible, circular ring disposed at the distal end of the push rod, the ring having diametrically opposite arcuate slots defined therein, the ring defining a circular cutting blade;
a conical rod sleeve having a wide diameter proximal end abutting the distal end of the housing and a narrow diameter distal end attached to and extending through one of the arcuate slots defined in the circular ring, the distal end of the push rod extending through the sleeve and engaging the diametrically opposite arcuate slot defined in the circular ring, the push rod collapsing and stretching the circular ring to fit through a small incision in a cornea of an eye when the push rod is slidably extended from the housing, the circular ring resiliently regaining a circular configuration facing an anterior capsule in the eye when the push rod is retracted; and
a pulley assembly having a roller disposed in the distal end of the housing and an elongated flexible filamentous element attached to the roller, extending through the rod sleeve, and looped around the circular ring, the circular cutting blade making a circular capsulotomy incision in the anterior capsule when the roller is alternately rotated clockwise and counterclockwise.

2. The circular capsulotomy incision tool according to claim 1, further comprising a slide button slidably mounted on said housing and connected to the proximal end of said push rod for extending and retracting the push rod.

3. The circular capsulotomy incision tool according to claim 1, wherein the distal end of said push rod is C-shaped, having a first leg insertable through the diametrically opposite arcuate slot defined in the circular ring and a second leg parallel to the first leg, the second leg extending over the circular ring so that the distal end of said push rod hooks the circular ring opposite the rod sleeve.

4. The circular capsulotomy incision tool according to claim 1, wherein the distal end of said rod sleeve has an annular notch defined therein, the notch snapping into one of the arcuate slots defined in the circular ring to attach the sleeve to the circular ring.

5. The circular capsulotomy incision tool according to claim 1, wherein said elongated flexible filamentous element comprises a string.

6. The circular capsulotomy incision tool according to claim 1, wherein said elongated flexible filamentous element comprises a wire.

7. The circular capsulotomy incision tool according to claim 1, wherein said roller further comprises an axle extending through the roller, the axle being mounted within said housing, said housing having a port defined therein for manually accessing and rotating the roller.

8. The circular capsulotomy incision tool according to claim 1, wherein the tool is made from disposable thermoplastic material.

9. The circular capsulotomy incision tool according to claim 1, wherein said resilient, collapsible, circular ring is made of nitinol.

* * * * *